US008932313B2

(12) United States Patent
Weiss et al.

(10) Patent No.: US 8,932,313 B2
(45) Date of Patent: Jan. 13, 2015

(54) BLOOD COLLECTION SYSTEM FOR COLLECTING BLOOD FROM A BODY PART FOR DIAGNOSTIC PURPOSES

(75) Inventors: Thomas Weiss, Mannheim (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1256 days.

(21) Appl. No.: 11/743,410

(22) Filed: May 2, 2007

(65) Prior Publication Data

US 2007/0260272 A1 Nov. 8, 2007

(30) Foreign Application Priority Data

May 4, 2006 (EP) ..................................... 06009200

(51) Int. Cl.
*A61B 17/32* (2006.01)
*A61B 5/15* (2006.01)

(52) U.S. Cl.
CPC .................................... *A61B 5/1411* (2013.01)
USPC ....................................................... 606/182

(58) Field of Classification Search
USPC .......... 600/573, 578, 583; 604/135, 136, 137; 606/181–183
See application file for complete search history.

(56) References Cited

U.S. PATENT DOCUMENTS

| 4,442,836 | A | | 4/1984 | Meinecke et al. |
| 4,527,561 | A | * | 7/1985 | Burns ........................... 606/182 |
| 4,553,541 | A | | 11/1985 | Burns |
| 4,577,630 | A | | 3/1986 | Nitzsche et al. |
| 4,653,513 | A | * | 3/1987 | Dombrowski ................ 600/578 |
| 4,869,249 | A | * | 9/1989 | Crossman et al. ............ 606/182 |
| 5,035,704 | A | * | 7/1991 | Lambert et al. ............... 606/182 |
| 5,122,119 | A | * | 6/1992 | Lucas ........................... 604/138 |
| 5,196,025 | A | * | 3/1993 | Ranalletta et al. ............ 606/182 |
| 5,954,738 | A | * | 9/1999 | LeVaughn et al. ............ 606/181 |
| 6,206,901 | B1 | | 3/2001 | Rutynowski et al. |
| 6,332,871 | B1 | | 12/2001 | Douglas et al. |

(Continued)

FOREIGN PATENT DOCUMENTS

| EP | 0 036 443 | 9/1981 |
| EP | 1 625 825 | 2/2006 |
| WO | WO 2005110226 A1 * | 11/2005 |

OTHER PUBLICATIONS www.thefreedictionary.com/tension, definitiion of the term "tension" retrieved Sep. 4, 2013.*

*Primary Examiner* — David Eastwood
(74) *Attorney, Agent, or Firm* — Bose McKinney & Evans LLP (57) ABSTRACT

A blood collection system for collecting blood from a body part for diagnostic purposes, comprising a housing with a lancet guide, by which a lancet is guided on a predetermined puncture path, and a lancet drive for driving a puncturing movement of the lancet on the predetermined puncture path. The puncturing movement comprises a forward movement phase in the direction of puncturing and, after reaching a reversal point, a subsequent retraction movement phase in the direction opposite the puncture direction. The lancet drive has a driving spring, which is arranged behind the lancet and is connected to the lancet during the forward movement phase of the puncturing movement so that the lancet is driven in the puncturing direction. The system comprises an oscillation control device for controlling oscillation of the lancet and the driving spring in such a manner that repeated puncturing of the body part by the lancet is prevented.

32 Claims, 6 Drawing Sheets

(56) References Cited

U.S. PATENT DOCUMENTS

| | | | |
|---|---|---|---|
| 8,109,960 B2* | 2/2012 | Sarna et al. | 606/182 |
| 8,221,441 B2* | 7/2012 | Dicesare et al. | 606/182 |
| 2001/0039387 A1* | 11/2001 | Rutynowski et al. | 600/573 |
| 2002/0029058 A1* | 3/2002 | Levaughn et al. | 606/181 |
| 2002/0082522 A1* | 6/2002 | Douglas et al. | 600/583 |
| 2003/0105430 A1* | 6/2003 | Lavi et al. | 604/136 |
| 2003/0187470 A1* | 10/2003 | Chelak et al. | 606/182 |
| 2004/0092996 A1* | 5/2004 | List et al. | 606/181 |
| 2004/0260326 A1* | 12/2004 | Lipoma et al. | 606/182 |
| 2004/0267300 A1 | 12/2004 | Mace | |
| 2005/0038465 A1* | 2/2005 | Shraga | 606/182 |
| 2005/0085840 A1* | 4/2005 | Yi et al. | 606/182 |
| 2006/0052809 A1* | 3/2006 | Karbowniczek et al. | 606/181 |

* cited by examiner

BLOOD COLLECTION SYSTEM FOR COLLECTING BLOOD FROM A BODY PART FOR DIAGNOSTIC PURPOSES

RELATED APPLICATIONS

This application claims priority to European Patent Application No. 06 009 200.4, filed May 4, 2006, which is hereby incorporated by reference.

BACKGROUND

The invention relates to a blood collection system for collecting blood from a body part for diagnostic purposes.

For analytical diagnostic purposes, a small amount of blood is collected from a body part. This is done by using lancets, the tip of which creates a wound in a body part, preferably a finger or an earlobe. This method of collecting blood is of great importance, especially as a self-collection system for diabetic self-monitoring because it permits a greatly improved method of stabilizing the medication treatment of diabetics. This also makes it possible to prevent the serious sequelae of diabetes.

Therefore, in the state of the art there have been proposals for a plurality of instruments and lancet devices with which the puncturing procedure is performed mechanically. Normally, a spring is used to drive the puncturing movement. The depth of penetration can be defined by a stop in the housing against which the lancet or a component of the lancet drive is stopped. However, the stopping causes a considerable oscillation which prevents a uniformly clean puncture.

It has been found that with the widely used devices in which the lancet is coupled to the driving spring during the entire puncturing movement, which is made up of a forward movement phase and a retraction movement phase, post-pulse oscillation of the spring results in the tip of the lancet puncturing the body part more than once. This is undesirable, however, because it causes the patient additional pain.

This problem does not exist with more complex designs with which the driving spring is coupled to the lancet only during the forward movement phase and an additional mechanism is provided for retracting the lancet from the body part.

For example, a blood collecting device with a lancet is known from U.S. Pat. No. 6,206,901 B1; in this patent, the lancet is driven by a ram and a driving spring. The lancet here is uncoupled from the driving spring for a part of its forward movement phase. To retract the lancet, a second spring is provided near an outlet opening in the housing. This second spring is designed as a return spring and serves to retract the lancet out of the wound after the puncture step. The return spring is put under tension by the lancet only during the forward movement phase. The kinetic energy of the lancet is stored in the spring and, after reaching the maximum stress of the return spring, the kinetic energy is returned to the lancet by the spring. However, this has the disadvantage that the lancet is decelerated by the return spring. Therefore, the entrance of the lancet into the patient's skin takes place painfully and slowly.

EP 0 036 443 B1 also discloses a lancet device with which a lancet is driven by a driving spring during the forward movement phase, and the driving spring is uncoupled from the lancet during a part of the puncturing movement. To return the lancet after the puncturing operation, a second spring is provided in the area of an opening in the housing of the lancet device, moving the lancet in the reverse direction after the puncturing operation. The second spring is put under tension by the lancet only during the forward movement phase of the puncturing movement, i.e., not before the lancet strikes the second spring on the movement path in the puncturing direction. Therefore, the lancet is decelerated; its kinetic energy is converted into spring energy until the kinetic energy is completely consumed. Then, the puncturing of the lancet into the body part is again decelerated.

US 2004/0267300 A1 discloses a lancet device with which the lancet is driven by a rotating spring having a plurality of spring arms. The spring arms are put under tension. After releasing a lock, the spring arms move the lancet in the direction of an opening in the housing. After releasing the tension on the spring arms, which are designed between an outer ring and an inner ring, there is no post-pulse oscillation. To move the lancet back out of its puncture position, restoring spring arms are provided. These arms are located between the inner ring and an inside axis. The restoring spring arms are put under tension before the start of the puncturing movement. As soon as the lancet has punctured into a body part, i.e., the spring arms are completely relaxed. The restoring spring arms are also relaxed, so that the lancet is retracted out of its puncture position. Since the restoring spring arms are already prestressed, no kinetic energy of the lancet is used for applying tension to the restoring springs during the puncture movement. The puncture is thus made rapidly and with little pain. However, the mechanism of the lancet device is very complicated because an accurate cooperation of the spring arms applying tension as well as the restoring spring arms must be ensured. In addition, the rotational movement of the springs must be converted to a translational movement of the lancet.

All these known blood collecting devices have a much more complicated structure than the designs mentioned in the introduction, where the spring (usually a simple helical spring) executes a releasing movement that acts linearly in the direction of puncture and is transmitted directly to the lancet. This design principle is not only simple and therefore inexpensive, but is also space saving. It therefore allows a slender construction for the hand which facilitates handling. To implement a rapid and therefore relatively pain-free puncture of the lancet in a body part, strong driving springs are used. There is a particularly great risk that the lancet, i.e., the lancet needle might puncture the body part repeatedly due to post-pulse oscillation of the driving spring. If the driving spring is designed to be weaker, the maximum puncture depth in the skin is not ensured, in which event not enough blood is obtained.

SUMMARY OF THE INVENTION

The present invention provides a blood collection system which is simple and at the same time provides rapid and pain-free puncture.

The blood collection system in exemplary embodiments comprises a housing having a lancet guide for guiding a lancet on a predetermined puncture path and a lancet drive for driving a puncture movement of the lancet on the predetermined puncture path. The puncture movement comprises a forward movement phase in the puncture direction and a retraction movement phase, which then follows at a reversal point, in the direction opposite the puncture direction. The lancet drive comprises a driving or drive spring which is positioned behind the lancet and is coupled to the lancet during the forward movement phase so that the relaxation movement of the driving spring drives the lancet directly (i.e., without any gear elements) during at least a part of the forward movement phase of the puncture movement. At the end of the forward movement phase, the tip of the lancet punctures the body part to create a wound. After reaching the reversal point, the lancet is retracted out of the skin in the retraction movement phase of the puncture movement.

In this blood collection system in which the driving spring is positioned behind the lancet, in particular coaxially behind the lancet, an oscillatory system is formed by the lancet and the one or more springs affecting the movement of the lancet. This oscillatory system can perform an oscillating movement forth and back in and against the puncturing direction between two reversal points. During the retraction movement phase of the lancet, the driving spring is in the return path of the lancet so that the lancet can act on the driving spring. Therefore, the energy of the lancet can be transmitted back to the driving spring and stored in it. The driving spring which is thereby under renewed tension can drive the lancet back in the puncture direction so that there is a risk of repeated punctures. According to exemplary embodiments of the invention, such a system is provided with an oscillation control device or mechanism that acts on the lancet during the retraction movement phase of the puncture movement. The oscillation control device is also referred to below with the abbreviation ROTOCOM (retraction operating oscillation control means).

The oscillation control device can act on the oscillation behavior of the lancet in essentially three ways. First, it can have a displaceable stop so that the oscillating movement of the lancet in the puncture direction is limited by the stop. The stop limits the oscillation, which then comes to a standstill more rapidly. The second possibility is damping the oscillation, so that there is a great reduction in oscillation amplitude. In the ideal case, the lancet can come to a standstill even during the first return. The third possibility is to provide a position displacement of the driving spring by means of which the zero point of the oscillation about which the driving spring oscillates is displaced against the direction of puncture in such a manner that even at maximum deflection of the driving spring, the lancet is prevented from puncturing the body part. The oscillation itself is not affected. Repeated back-and-forth oscillation is possible.

All three embodiments have in common the fact that the oscillation of the lancet is controlled by the oscillation control device, so that repeated puncturing of the body part with the lancet is prevented.

By means of the ROTCOM system acting on the lancet during the retraction movement phase, and in exemplary embodiments only then, repeated puncturing of the skin is prevented while at the same time the advantages associated with the coaxial arrangement of the driving spring behind the lancet are preserved, especially with regard to simple design.

In the context of the present invention, it has been found that the use of the ROTOCOM system leads to other important advantages:

The ROTOCOM system acts on the lancet during the retraction movement phase but not substantially during the forward movement phase. The forward movement phase therefore remains substantially unaffected. Consequently, the lancet can puncture the body part at a high speed so that the patient perceives only relatively minor pain.

The adjustment of the depth of puncturing of the lancet into the body part is independent of the oscillation control device. No additional design measures need be taken to compensate for or rule out a possible influence from adjusting puncture depth.

Complex designs that provide for uncoupling of the drive mechanics from the lancet during the retraction movement phase and which therefore must have a separate return mechanism can be replaced by systems having a simple and therefore inexpensive design. In these systems, the lancet is driven directly by the spring without a gear, and in particular is coupled to the spring during the entire puncturing movement, i.e., during the forward movement phase and the retraction movement phase.

According to certain embodiments, the oscillation control device comprises a movable end stop to prevent repeated punctures. The end stop is shifted against the direction of puncturing into a holding position after the lancet reaches the reversal point in the puncturing movement. Therefore, in post-pulse oscillation the path of the lancet is limited in the puncture direction. Before the start of the puncture, the movable end stop is held in a starting position in which it has no effect on the puncturing procedure and does not influence the puncture movement. Only after reaching the reversal point of the puncture movement the end stop is moved from the starting position into the holding position. In case of a renewed oscillation of the lancet in the puncture direction the end stop acts on the lancet and thereby limits the path of the lancet in the puncture direction, i.e., the end stop limits the post-pulse oscillating movement of the lancet.

The end stop is preferably secured in the holding position. Therefore, reliable limitation of the movement of the lancet is achieved; displacement of the end stop by the lancet moving again in the puncture direction is ruled out by the locking of the end stop. This can be implemented by means of a hook, for example.

A stop spring is provided in one embodiment for displacing the end stop into the holding position. The stop spring moves the end stop out of its starting position into the holding position. So, the stop spring is prestressed and the end stop is locked in its starting position. The stop spring is thus already prestressed during the puncturing movement in the puncture direction of the lancet. The locking of the stop spring may be released at the end of the forward movement phase of the puncturing movement. The end stop is moved in the direction opposite the puncture direction. When this movement in which the spring energy is converted into kinetic energy, the lancet can be additionally driven during the retraction movement phase. Therefore, the retraction movement phase can be accelerated.

The blood collection system according to the invention in certain embodiments comprises a tension device tensioning the stop spring. The tension device has a threaded rod with a thread and a tension element. By rotating the threaded rod, the tension element is moved along the rod, entraining the stop spring with it. The tension element is guided on a guide surface during its tension movement. The guide surface reliably prevents the tension element from also rotating with the threaded rod. In this manner, the rotational movement of the threaded rod is converted into a translational movement so that the stop spring, which may be a spiral spring, is stretched or compressed out of its resting position. The energy applied by the tension element and the threaded rod is stored in the spring. The spring is then locked in the tense state, so that the stored energy of the spring is retained. Only after releasing the lock the spring energy is transformed back into kinetic energy.

The guide surface for guiding the tension element can be formed as an edge running parallel to the threaded rod. Alternatively, the guide surface can be formed as a groove or a shoulder in the housing, for example.

After reaching the starting position of the stop spring in which it is under tension, the tension element is guided on a return edge in its movement in the direction opposite the direction of movement for tensioning. The guidance on the return edge is accomplished in such a manner that the tension element will be disengaged from the stop spring. Therefore, the tension element is rotated into a position in which it is in contact with the return edge. In this position, the stop spring can move after releasing the lock without colliding with the tension element.

When the blood collection system is designed as a so-called single-use device, i.e., as a disposable puncture device, the stop spring can already be prestressed at the time of assembly and can be installed in the prestressed state. The stop spring and/or the prestressed end stop must then be merely released at the reversal point of the puncturing movement so that the end stop is moved against the puncture direction. In this case a tension device can be omitted.

According to another embodiment, the ROTOCOM system has a damping device for decelerating the movement of the lancet in the retraction movement phase. Consequently, the lancet executes a dampened movement during the retraction movement phase. Damping is understood here to refer to a reduction in amplitude of an oscillation (here the post-pulse oscillation of the lancet) which is caused by a loss of energy. The loss of energy is the transition of the oscillation energy into another energy form. The kinetic energy of the lancet is rapidly converted by the damping device into another form of energy. In the ideal case, the lancet is very rapidly decelerated to a complete standstill during the retraction movement phase and post-pulse oscillation is completely prevented. The lancet should be moved against the puncture direction at least to the extent that the tip of the lancet is removed from the wound in the body part.

The damping device may be designed as a pneumatic damper. The damper can be equipped with a plunger, for example, and a pressure chamber, whereby the plunger compresses the air present in the pressure chamber during the retraction movement phase of the lancet and the air is released through the throttle point so that energy is withdrawn from the system.

Therefore, a coupling element can be provided between the lancet and the driving spring. The coupling element is guided in a cylinder which can be a part of the housing of the blood collection system, for example. Preferably, sealing lips are arranged on the coupling element, these lips being in contact with the inner wall of the cylinder. Thus, the damping system operates according to the principle of an air pump, wherein the sealing lips of the coupling element are arranged in such a manner that with movement of the coupling element in one direction, air can flow by, but in the opposite direction air cannot flow by. The use of the sealing lips proves to be a simple principle but is very efficient. In addition, sealing lips can also be mounted on the coupling element very easily, e.g., by means of a groove in the case of a coupling element having a round cross section.

In another preferred embodiment, the sealing lips of the coupling element are in contact with the inner wall of the cylinder in such a manner that the lancet is not significantly decelerated (i.e., the puncturing movement of the lancet in the forward movement phase is not influenced to a relevant extent). The lancet can penetrate into the body part at a high speed.

Through suitable arrangement of the sealing lips of the coupling element, the air contained in the cylinder before the sealing lips is compressed during the retraction movement phase of the lancet. This causes the lancet to be retarded in its retraction movement phase. Post-pulse oscillation is effectively prevented by either dissipating the heat of compression during compression, e.g., via the cylinder walls and/or blowing out the compressed air through a throttle site. In addition, the sealing lips are pressed by the rising air pressure against the cylinder wall, thus causing increased friction. Retardation of the lancet can be optimized through the choice of the angle of inclination of the sealing lips with respect to the cylinder wall so that the path passed by the lancet during the retraction movement phase can be predetermined. At the same time, the influence on the lancet during the forward movement phase of the puncturing movement can be ascertained through the angle of inclination of the lips. The damping behavior of the damping system can be determined through a suitable choice of the material of the sealing lips, their hardness and elasticity.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 6b shows an enlarged detail from FIG. 6a;

FIG. 6c shows an enlarged detail from FIG. 6a; and

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
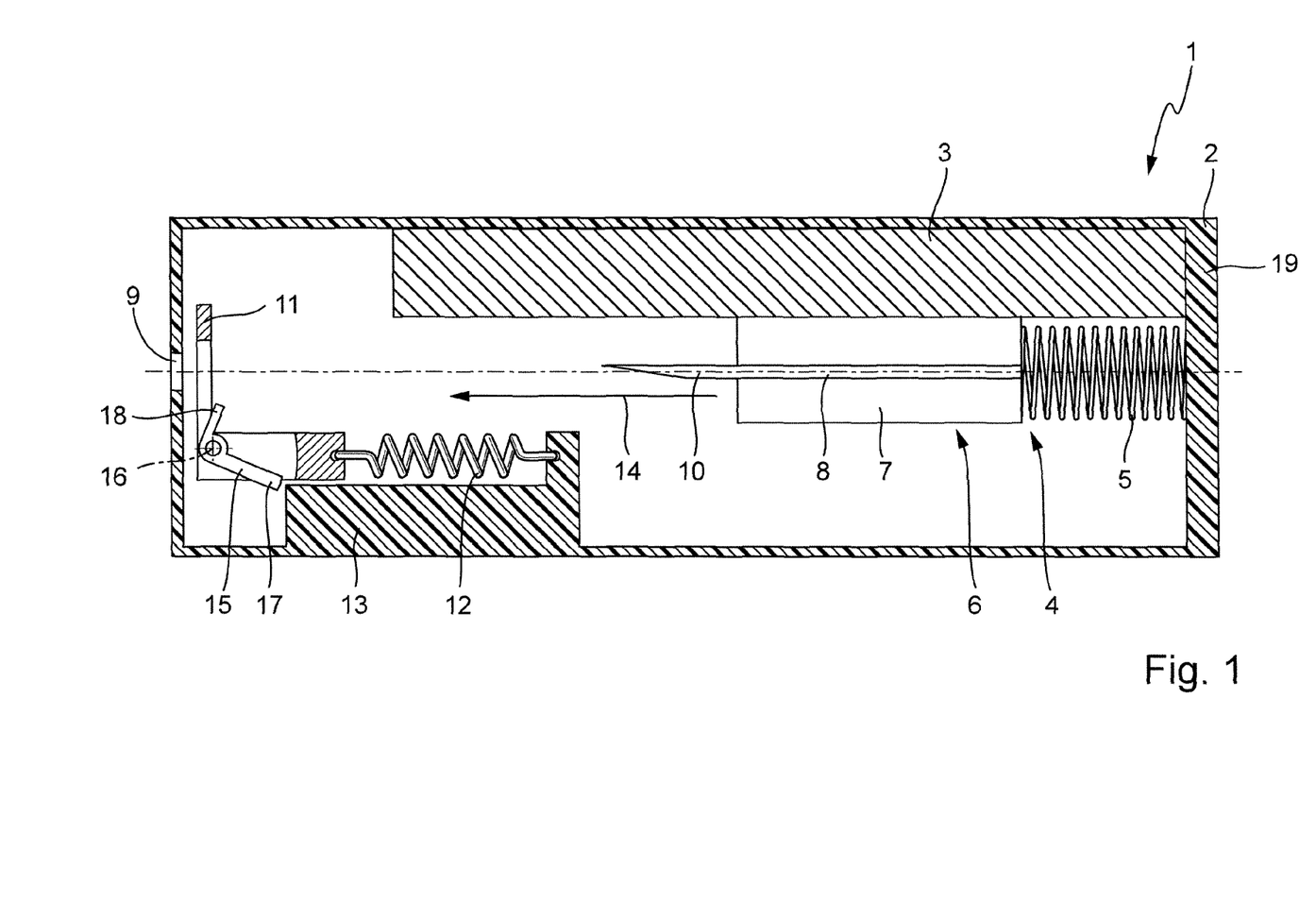
FIG. 1 is a side sectional view of an inventive blood collection system having an end stop during the forward movement phase of a puncturing movement of a lancet.
Figure 2:
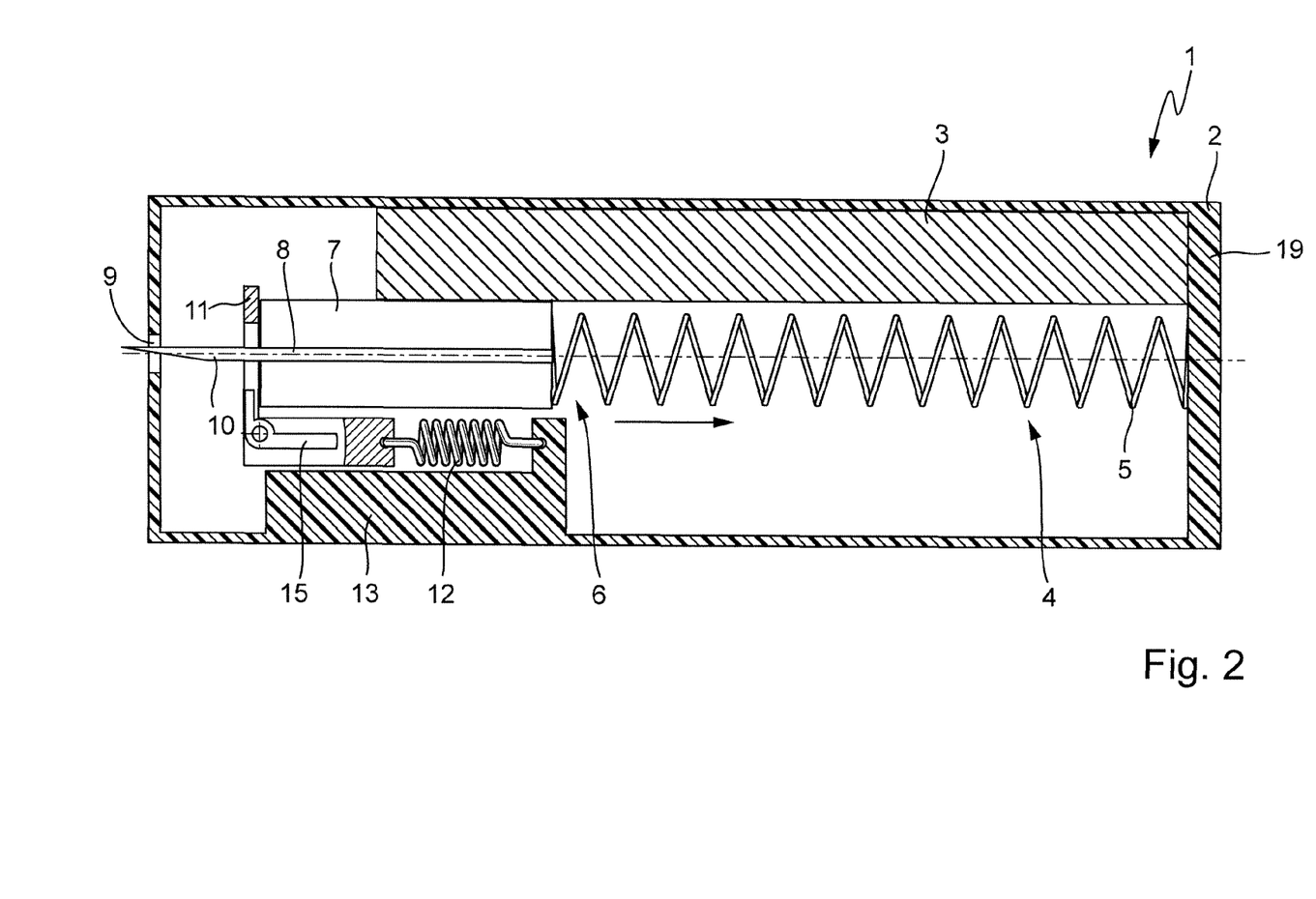
FIG. 2 is a sectional view of the blood collection system from FIG. 1 during the retraction movement phase of the puncturing movement.

FIGS. 1 and 2 show an embodiment of a blood collection system 1 in a longitudinal section. The blood collection system 1 includes a housing 2 with a lancet guide 3 and a lancet drive 4 coupled to the housing 2. The lancet drive 4 comprises a driving spring 5 and a coupling element 6 which is designed as a lancet holder 7. A lancet 8 is held in the lancet holder 7.

The housing 2 has an opening 9 on a front end through which the lancet 8 can emerge from the housing 2 and create a wound in a body part. Alternatively, the opening 9 can also be larger, so that the skin of the body part with which the housing 2 is in contact protrudes into the opening 9. The lancet 8 then need not emerge from the housing 2 to create a wound.

The housing 2 also comprises an end stop 11 which is coupled to a stop holder 13 via a stop spring 12. The stop holder 13 is fixedly connected to the housing 2. At the same time, it guides the end stop 11.

FIG. 1 shows the blood collection system 1 during the forward movement phase of the puncturing movement of the lancet. The driving spring 5 had been prestressed and is now moving the lancet 8 in the puncture direction, which is represented by the arrow 14.

The end stop 11 is shown in its starting position. A lock designed as a latch 15 holds the end stop 11 in its starting position. The latch 15 is mounted to rotate about a rotating bearing 16 on the end stop 11. The latch has an L shape form with a long L-leg 17 and a short L-leg 18. The long L-leg 17 is in contact with the stop holder 13 at its free end so that the end stop 11 is locked. The stop spring 12 is prestressed. The spring is preferably a tension spring, as shown in the example.

During the forward movement phase of the puncturing movement, the lancet 8 is moved in the direction of the opening 9, i.e., in the puncturing direction. At the end of the forward movement phase, the lancet 8 strikes the short L-leg 18 of the latch 15 and rotates the latch 15 counterclockwise. This results in the long L-leg 17 becoming disengaged from the stop holder 13 so that the end stop 11 is no longer locked. At this moment the lancet 8 has reached the reversal point in its puncturing movement and is pulled back in the direction of the housing end 19 by the driving spring 5.

At the same time, during the retraction movement phase of the puncturing movement of the lancet 8, the end stop 11 is moved from its starting position opposite the puncturing direction (FIG. 2). So, the tensioned stop spring 12 contracts so that the end stop 11 is moved opposite the puncturing direction until the end stop 11 has reached its holding position.

During the movement of the end stop 11, the end stop 11 is preferably in contact with the lancet 8 so that the lancet 8 is not only moved by the driving spring 5 during the retraction movement phase of the puncturing movement but is (also) moved indirectly by the stop spring 12. In this manner, the retraction speed can be designed independently of the propulsion and/or the lancet 8 can be accelerated.

As soon as the end stop 11 has reached its holding position, it is preferably pressed against a stop on the guide 13 by the residual tension in the stop spring 12, so that the end stop forms a fixed stop for the lancet 8 at the distal end. This prevents the lancet 8, which remains in or picks up again the interaction with the driving spring, from advancing farther than the end stop. The end stop 11 is then secured in its holding position. Then, the lancet 8 is moved only by the driving spring 5 (opposite the puncturing direction).

Alternatively, the end stop 11 is held elastically in its holding position. It is not secured but instead is held only by the stop spring 12. Thus, the end stop 11 can oscillate around the holding position with a small amplitude.

The stop spring 12 can be prestressed. In particular, it can be still prestressed when the end stop 11 is displaced in its holding position. The stop spring 12 in this case would have a high prestressing force which can be achieved, for example, by a high spring constant or by a large deflection when the spring constant is low. Then, the end stop 11 can move about its holding position only with a small amplitude even if the lancet 8 is being moved back in the puncturing direction by the driving spring 12 in the post-pulse oscillation and the lancet 8 exerts a force on the end stop 11 in the direction of the opening 9.

In the holding position of the end stop 11, the distance between the end stop 11 and the opening 9 must be larger than the length of the tip 10 of the lancet 8 so that the tip 10 does not pass through the opening 9 in the housing 2 to the outside. The distance between the end stop 11 and the opening 9 in the holding position is preferably so large that the lancet tip does not emerge from the opening 9 despite the oscillation of the end stop 11 about the holding position (with a small amplitude, which is determined by the spring constant of the stop spring 12).

The depth of puncture of the lancet 8 can be adjusted variably through the starting position of the end stop 11. Therefore, the end stop 11 can also serve at the same time to adjust the depth of puncture of the tip 10 of the lancet 8.

Figure 3:
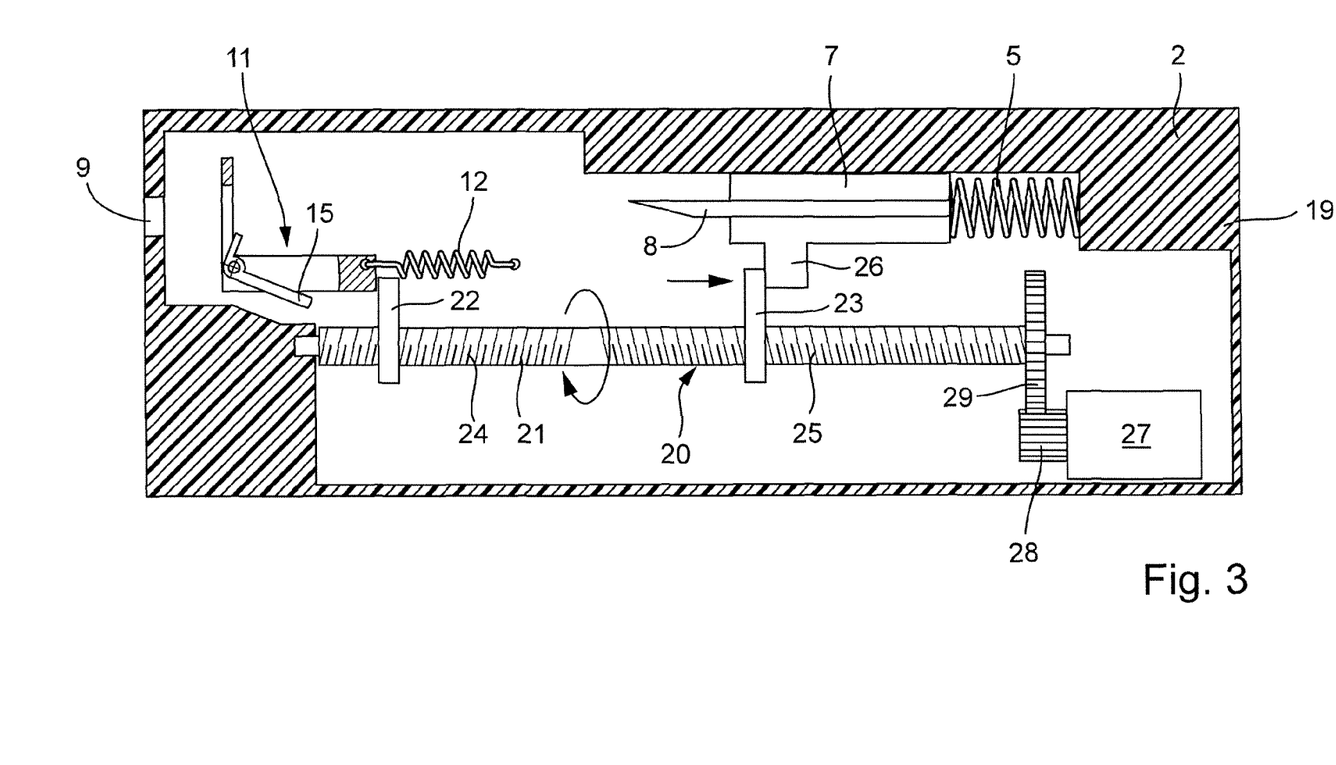
FIG. 3 is a sectional view showing an alternative embodiment of the blood collection system with a threaded rod for moving the end stop into a starting position and for tensioning a driving spring of the lancet.

FIG. 3 shows a schematic diagram of an alternative embodiment of a blood collection system with a housing 2 and an opening 9. A first embodiment of a tensioning device 20 for applying tension to the driving spring 5 and the stop spring 12 is illustrated. The tensioning device 20 comprises a threaded rod 21 with a first tension element 22 for tensioning the stop spring 12 and a second tension element 23 for tensioning to the drive spring 5. The threaded rod 21 has two opposing threads 24, 25, wherein the first thread 24 moves the first tension element 22 and the second thread 25 moves the second tension element 23.

In the example shown in FIG. 3, by turning the threaded rod 21 clockwise, the tension element 22 is moved in the direction of the opening 9 of the housing, while at the same time, the tension element 23 is moved in the direction of the end 19 of the housing. During the movement of the threaded rod 21, the first tension element 22 acts directly on the end stop 11, moving it out of its holding position into its starting position. The latch 15 engages on the stop holder 13 (not shown in FIG. 3) so that the end stop 11 is held in its starting position. The second tension element 23 which is moved by the thread 25 acts on an entraining element 26 on the lancet holder 7. In this manner the lancet holder 7 is shifted together with the lancet 8 opposite the puncturing direction and the driving spring 5 is put under tension. Here also a lock (not shown) is provided, holding the lancet 8 in its stressed position. When this lock is released, the puncturing movement of the lancet 8 begins, causing the lancet 8 to move in the puncturing direction.

The latch 15 is only one possibility for locking the end stop 11 in its starting position and/or releasing it from this position. Of course, any other locks can be used to secure the end stop 11 in its starting position. In particular, a lock can be provided which is not released by the lancet 8 or the lancet holder 7 until traveling a certain distance during the retraction movement phase of the puncturing movement, so that the end stop 11 remains in its starting position even at the beginning of the retraction movement phase of the puncturing movement of the lancet 8.

The two threads 24 and 25 can have different pitches and different lengths taking into account the possibility that the driving spring 5 and the stop spring 12 have different spring constants and sizes. Consequently, the tension paths of the end stop 11 and the lancet holder 7 are different.

The threaded rod 21 can be driven mechanically by a crank or some other mechanism or can be driven electrically as illustrated in FIG. 3. A motor 27 drives a second gearwheel 29 that is rigidly connected to the threaded rod 21 via a gearwheel 28. The rotation of the motor 27 in one direction causes a corresponding rotation of the threaded rod 21 and thus a displacement of the tension elements 22 and 23.

After the driving spring 5 and the stop spring 12 have been tensioned by the tension device 20, the tension elements 22 and 23 can be moved back in the direction of the center of the threaded rod 21, i.e., toward one another. So, guidance of the tension elements 22 and 23 is necessary as in the tensioning movement. Guidance during the tensioning movement is provided by a guide surface 30 which are in contact with the tension element. The retraction, i.e., the movement of the tension elements in the direction opposite the direction of movement for tensioning is initiated by a return edge 31.

Figure 4:
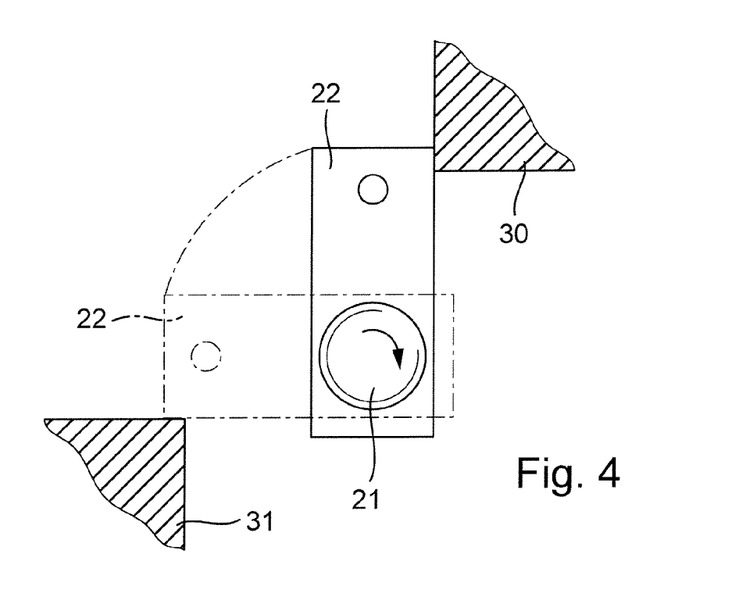
FIG. 4 is a fragmentary cross-sectional view through the threaded rod from FIG. 3.

FIG. 4 shows the threaded rod 21 in cross section with a tension element 22 in two positions. In the position of tension element 22 shown with dotted lines, the tension element 22 is in contact with the return edge 31. Moving the threaded rod counterclockwise, causes the tension element 22 to rotate along with the threaded rod until the tension element rests against the return edge 31. The tension element is then shifted along the return edge 31 and the threaded rod 21. In this position the tension element 22 is not in the path of movement of the end stop 11.

By rotating the threaded rod clockwise, the tension element 22 is also rotated clockwise until it comes to a stop against the guide face 30. Further rotation of the threaded rod 21 causes the tension element 22 to execute a translational movement into the plane of the drawing along the guide face 30. Due to this translational movement, the stop spring 12 of the end stop 11 shown in FIG. 3 is put under tension.

The schematic diagram shown in FIG. 4 with the tension element 22 is also applicable for the tension element 23. The tension element 23 is also guided along the guide face 30 and/or the return edge 31 during the movement of the threaded rod 21. After putting the driving spring 5 of the lancet holder 7 under tension, the tension element 23 is in contact with the return edge 31 when it is moved in the direction of the middle of the threaded rod 21. In this position of the tension element 23, the lancet 8 together with the lancet holder 7 and the entraining element 26 can execute puncturing movements in the puncturing direction without having the entraining element 26 collide against the tension element 23.

Figure 5:
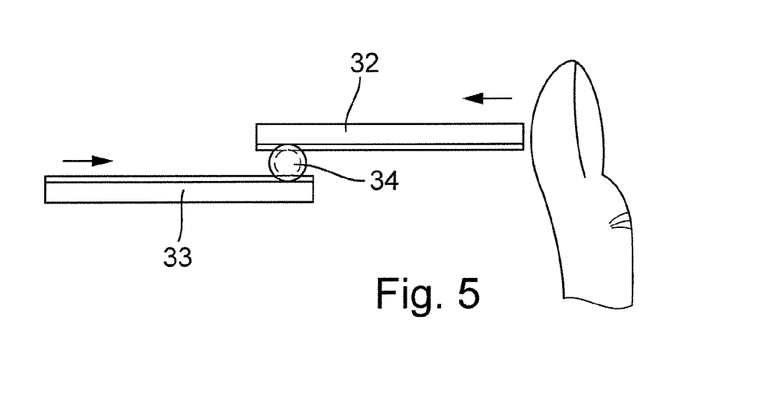
FIG. 5 shows a schematic basic diagram of an alternative tensioning device for the lancet and the end stop.

FIG. 5 shows a schematic diagram of an alternative tensioning device with which the driving spring 5 of the lancet holder 7 and the stop spring 12 of the end stop 11 can be put under tension simultaneously. It comprises a first toothed rack 32 and a second toothed rack 33 which are connected together by a gearwheel 34. The toothed rack 32 is coupled to the end stop (not shown). The toothed rack 33 is connected to the coupling element between the lancet and the driving spring. Moving the toothed rack 32 causes a movement of the toothed rack 33 indirectly over the gearwheel 34, so that in tensioning the end stop, the lancet is indirectly also put under tension. The two toothed racks 32 and 33 thus replace the threaded rod 21 from FIG. 3.

The entraining element 26 of the lancet holder 7 and the end stop 11 from FIG. 3 must of course be adapted to the toothed racks 32 and/or 33 in such a manner that the respective entraining elements are removed from the operating path of the end stop and/or the lancet. This can be accomplished, for example, by the fact that the toothed racks each have entraining elements on plate springs or on other elastic elements, and a ramp in the rack and/or in the housing deflects the entraining elements at the beginning of the tensioning movement. After retraction of the toothed racks 32 and 33 into a neutral position, the entraining elements spring out of the operating path of the lancet and the end stop.

Figure 6A:
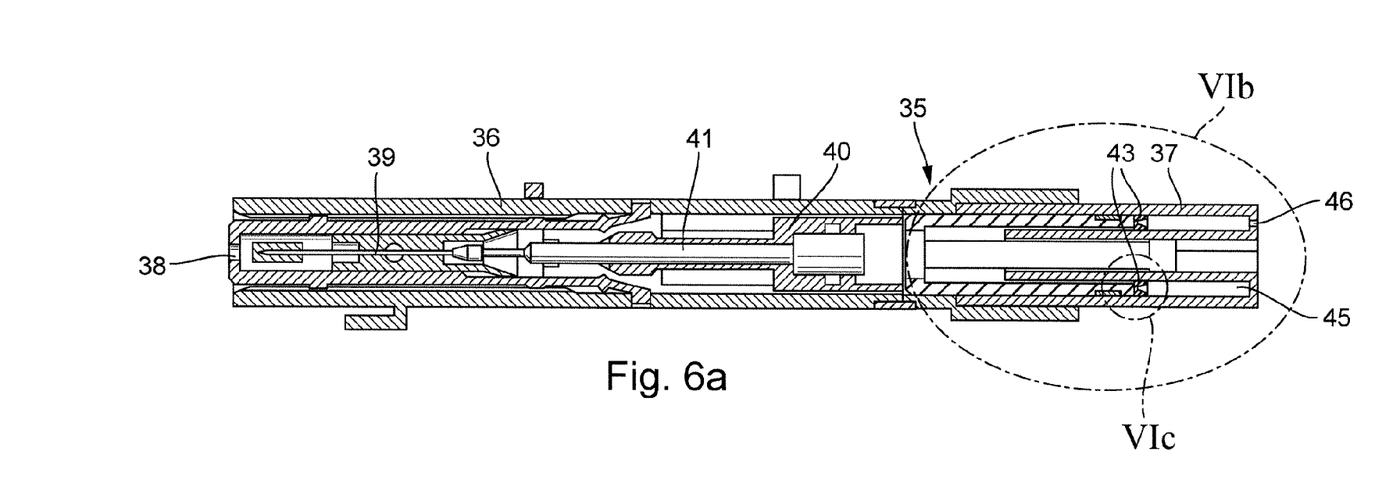
FIG. 6a is a sectional view of an alternative embodiment of a blood collection system with a damping device comprising a pneumatic damper.
Figure 6B:
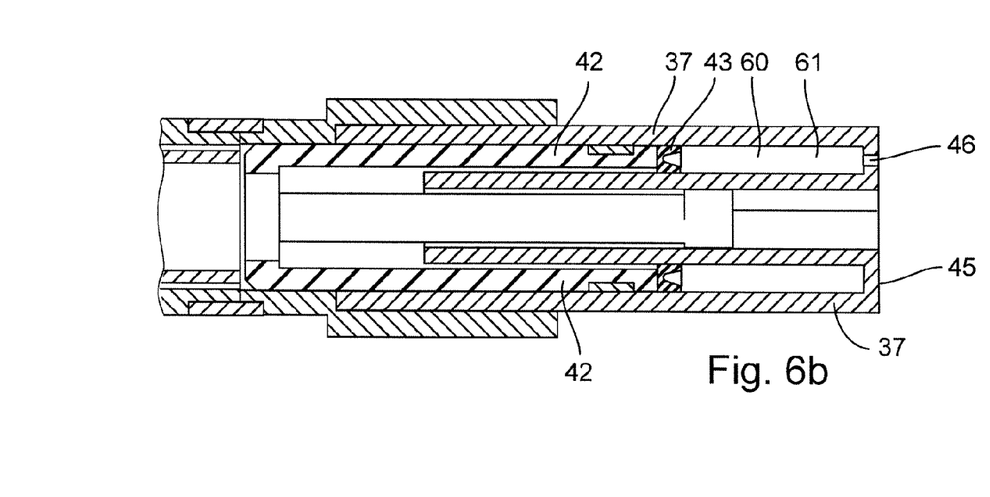
Figure 6C:
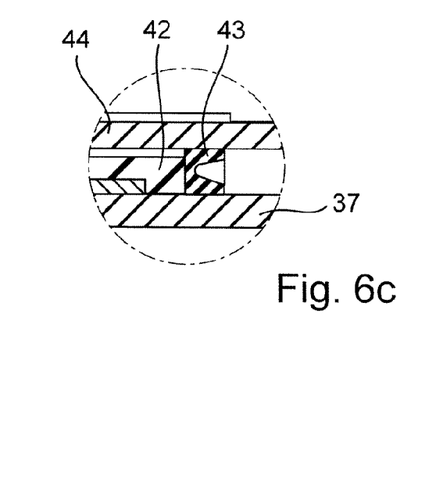

FIGS. 6a, 6b and 6c show an alternative embodiment of the inventive blood collection system. The oscillation control device in this embodiment is designed as a damping device 35 for damping and thus decelerating the movement of a lancet 39. The blood collection system shown in FIG. 6a comprises a housing 36 that is essentially cylindrical. The system comprises a damping cylinder 37 that forms one end of the housing 36. On the opposite end, the housing 36 has an opening 38 through which a lancet 39 guided in the housing 36 can emerge. The lancet 39 is coupled to a coupling element 40 that surrounds a drive ram 41. The coupling element 40 is connected to a driving spring (not shown) so that the lancet 39 is coupled to the driving spring during the puncturing movement. The lancet 39 is driven by the driving spring during the forward movement phase and during the retraction movement phase of the puncturing movement.

On its end facing away from the lancet 39, the coupling element 40 comprises a plunger 42 (FIG. 6b), which is a cylindrical sleeve with a large wall thickness, as shown in the diagram. The plunger 42 is guided in a groove 60. The groove 60 is arranged in the damping cylinder 37 which represents a double-walled cylinder when seen from its rear wall 45. The groove 60 is designed as a ring gap so that the plunger 42 is guided between an inner wall 44 of the damping cylinder and the outer wall of the damping cylinder. A gasket formed as a double sealing lip 43 is provided on the rear end of the plunger 42. The sealing lip is preferably made of a rubber-like material that is in contact with the outer wall of the damping cylinder 37 as well as the inner wall 44. These sealing lips are inclined against the two walls, so that with a forward movement of the plunger 42 in the puncturing direction, i.e., during the forward movement phase of the puncturing movement of the lancet 39, the sealing lips are in no contact or only in loose contact with the inner wall 44 and the damping cylinder 37. The air in the housing 36 can flow past the sealing lips 43 almost unchanged and is introduced into the damping cylinder 37, in particular into a compression compartment 61 between the rear wall 45 and the plunger 42. The compression compartment 61 is designed as a toroidal space due to the cylindrical design of the housing 36. The plunger 42 which is designed in the form of a sleeve can also be designed as a simple plunger which runs in a simple cylinder. The basic operation of such a plunger and cylinder is identical to that described above.

After reaching the reversal point in the puncturing movement, the lancet 39 is retracted back into the housing 36 by the driving spring in the subsequent retraction movement phase of the puncturing movement. The sealing lips 43, which are inclined slightly, are pressed tightly against the inner wall 44 and the damping cylinder 37 during the movement of the coupling element 40. The air in the toroidal compression compartment 61 can no longer flow between the sealing lips 43 and the inner wall 44 and/or the damping cylinder 37. The air in the compression compartment 61 is therefore compressed during the retraction movement phase of the puncturing movement. The ring gap and/or the groove 60 is sealed almost completely. The heat of compression generated during compression is diverted to the adjacent components.

In the compression compartment 61, an outflow opening 46 through which the air can escape is preferably provided on a rear wall 45. However, the diameter of the outflow opening 46 is so small that the air in the damping cylinder 37 is compressed. Therefore, energy is therefore withdrawn from the system and, in particular, the oscillation energy of the driving spring of the lancet 39 is used for compressing the air. The movement of the lancet 39 is greatly decelerated. Through a suitable choice of the geometry and size of the damping cylinder 37 and the diameter of the outflow opening 46, the damping of the entire system is determined. The diameter of the outflow opening 46 can advantageously be selected in such a manner that the lancet 39 is decelerated to a standstill even during the first retraction movement phase of the puncturing movement. Post-pulse oscillation of the lancet 39 is reliably prevented.

The outflow opening 46 is to be dimensioned in such a manner that the outlet resistance is not too low because otherwise the damping effect is low. On the other hand the flow resistance must not be too great because otherwise a pneumatic spring is formed rather than a damping. The parameters to be adapted here comprise the moving mass, the spring constant for forward movement and retraction movement, the movement strokes, the volume of the damping cylinder 37, the flow resistance of the outflow opening 46 and the friction factor of the sealing lip 43 on the inner wall 44 and the damping cylinder 37. The quantities cannot all be freely selectable, but they can be coordinated experimentally so that the desired effect is achieved. For example, the larger the moving mass, the greater must be the volume in the damping cylinder. The longer the movement stroke, i.e., the distance traveled by the lancet 39 and/or the coupling element 40, the smaller flow resistance should be set.

Figure 7:
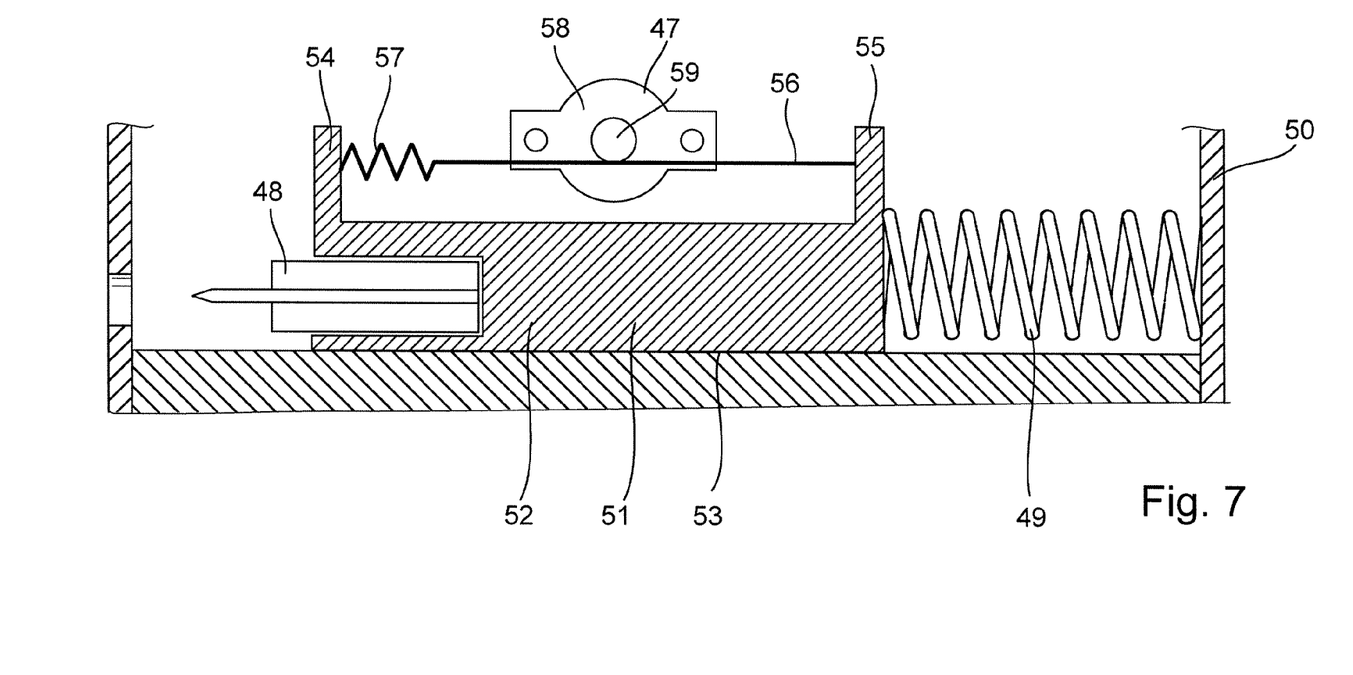
FIG. 7 shows a schematic diagram of a coupling element for a lancet with a hydraulic damper.

FIG. 7 shows an alternative embodiment of a damping system as a schematic diagram. Contrary to the embodiment according to FIG. 6a, the damping system here is not implemented as a pneumatic damper. In the system shown in FIG. 7, the damping system operates with a hydraulic damper 47. A lancet 48 is driven by a driving spring 49 coupled to a housing 50. A coupling element 51 designed as a lancet holder 52 is provided between the driving spring 49 and the lancet 48. The coupling element 51 is guided in a linear path on a linear guide 53 so that the puncturing movement is a linear movement during the forward movement phase and the retraction movement phase.

The coupling element 51 has a web 54 and another web 55 on its upper and lower ends, respectively. The two webs 54 and 55 together with the side wall of the coupling element 51 form a U shape. Between the upper web 54 and the lower web 55 a string 56 or card is stretched and is directly connected to the lower web 55. A tension spring 57 is provided between the upper web 54 and the string 56. The hydraulic damper 47 which is designed as a rotational damper 58 is arranged between the two webs 54 and 55. The rotational damper 58 comprises a shaft 59. The string 56 is wound with a plurality of turns around the shaft 59. The string 56 therefore has a friction factor $\mu$ with respect to the shaft 59 of the rotational damper 58. During the movement of the coupling element 51 the string 56 is pulled tightly with a force $F_0$ by the tension spring 57.

If the coupling element 51 is released from the stressed position (i.e., the position in which the driving spring 49 is under tension), the driving spring 49 drives the coupling element 51 and the lancet 48 forward so that the tip of the lancet 48 can emerge from an opening in the housing 50 of the blood collection system.

During the forward movement phase of the puncturing movement of the lancet 48, the rear end of the string 56 is released while the tension spring 57 is put further under tension. Therefore, the tensile force acting on the string 56 drops to a minimal level. As a result the string 56 slips on the shaft 59 of the rotational damper 58 during the forward movement phase of the puncturing movement of the lancet 48 and is decelerated with only a very low frictional force.

After reaching the reversal point in the puncturing movement, a tensile force acts on the rear end of the string 56 via the lower web 55 of the coupling element 51. The tension spring 57 keeps the string 56 taut. Thus, a force $F'=F_0 \cdot e^{\mu \alpha}$ can be transferred to the shaft 59 of the damper, where $\alpha$ denotes the angle of wrap which is obtained from the number of turns of the string 56 around the shaft 59 of the rotational damper 58 multiplied times 360°. If the tension spring 57 is dimensioned accordingly, the shaft 59 of the rotational damper 58 rotates with the movement of the coupling element 51 during the retraction movement phase of the puncturing movement and thus decelerates the movement of the lancet 48 to a desired predetermined low speed. This reliably prevents post-pulse oscillation of the coupling element 51 due to the driving spring 49. It is impossible for the lancet 48 to reemerge from the housing. Repeated puncturing of the body part is ruled out.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A blood collection system for collecting blood from a body part for diagnostic purposes, comprising:
    a housing having a lancet guide configured to guide a lancet,
    a lancet drive configured to drive a puncture movement of the lancet, the puncture movement comprising a forward movement in a puncture direction, a reversal point, and a subsequent retraction movement in the direction opposite the puncture direction;
    the lancet drive comprising a drive spring arranged behind the lancet, wherein during the forward movement the drive spring is connected to the lancet to drive the lancet in the puncture direction and wherein the drive spring contracts during the retraction movement, further wherein the lancet is automatically pulled back in the retraction movement by the drive spring immediately upon reaching the reversal point; and
    an oscillation control device configured to control oscillation of the lancet after the lancet reaches the reversal point, wherein, at the end of the forward movement, a latch of the oscillation control device is disengaged, thereby actuating the oscillation control device, wherein the forward movement of the lancet before puncture is substantially unaffected by the oscillation control device, the oscillation control device configured to prevent repeated puncturing of the body part by the lancet.

2. The blood collection system of claim 1, wherein the oscillation control device comprises a movable end stop which is configured to shift into a holding position after the lancet has reached the reversal point.

3. The blood collection system of claim 2, further comprising a fixing device for securing the end stop in the holding position.

4. The blood collection system of claim 2, further comprising an elastic device for moving the end stop toward the holding position.

5. The blood collection system of claim 2, further comprising a stop spring for displacing the end stop into the holding position.

6. The blood collection system of claim 5, wherein, during the puncturing movement of the lancet in the puncture direction, the stop spring is pre-stressed and locked, further wherein the stop spring is released at the end of the forward movement of the lancet.

7. The blood collection system of claim 5, wherein the stop spring has a residual tension when the end stop is in the holding position.

8. The blood collection system of claim 5, further comprising a tensioning device configured to apply tension to the stop spring, the tensioning device comprising a threaded rod with a thread and a first tension element that is moved by rotation of the threaded rod, the first tension element configured to be guided on a guide face during its movement to apply tension to the stop spring.

9. The blood collection of claim 8, wherein the threaded rod has first and second threads running in opposite directions and configured to move the first tension element and a second tension element, respectively, wherein the first tension element applies tension to the stop spring and the second tension element applies tension to the drive spring, whereby the stop spring and the drive spring are configured to be tensioned simultaneously.

10. The blood collection of claim 9, wherein the first thread and the second thread have different pitches.

11. The blood collection system of claim 8, wherein the first tension element is guided on a return edge in its movement opposite the direction of movement for applying tension and becomes disengaged from the stop spring.

12. A method of reducing lancet oscillation after puncture in the blood collection device of claim 1, the method comprising:
    releasing tension in the drive spring and thereby driving the lancet in the puncture direction to puncture a body part;
    allowing the lancet to reach the reversal point after which it is retracted by the drive spring in a retraction direction substantially opposite the puncture direction; and
    after the lancet reaches the reversal point, applying the oscillation control device to the lancet to prevent repeated puncturing of the body part by the lancet, wherein the driving of the lancet in the puncture direction is substantially unaffected by the oscillation control device.

13. The method of claim 12, wherein the applying the oscillation control device comprises releasing a displaceable stop that limits movement of the lancet in the puncture direction.

14. The method of claim 13, wherein the stop when released is displaced by a stop spring to which the stop is connected.

15. The method of claim 13, further comprising moving the stop to a holding position.

16. The method of claim 15, further comprising locking the stop in the holding position.

17. The method of claim 13, wherein the releasing the displaceable stop comprises contacting the stop with a lancet holder.

18. A blood collection system for collecting blood from a body part for diagnostic purposes, comprising:
    a housing having a lancet guide configured to guide a lancet;
    a drive spring disposed in the housing and configured to reciprocate the lancet in a puncture movement, the puncture movement comprising a forward movement in a puncture direction, a reversal point, and a subsequent retraction movement in the direction opposite the puncture direction, wherein the drive spring contracts during the retraction movement, further wherein the lancet is automatically pulled back in the retraction movement by the drive spring immediately upon reaching the reversal point; and
    an oscillation control device configured to control oscillation of the lancet after puncture, the oscillation control device comprising a movable end stop wherein, at the end of the forward movement, a latch of the oscillation control device is disengaged, thereby actuating the oscillation control device, wherein the forward movement of the lancet before puncture is substantially unaffected by the oscillation control device, the oscillation control device configured to prevent repeated puncturing of the body part by the lancet.

19. The blood collection system of claim 18, wherein the oscillation control device comprises a movable end stop which is configured to shift into a holding position after the lancet has reached the reversal point.

20. The blood collection system of claim 19, further comprising a fixing device for securing the end stop in its holding position.

21. The blood collection system of claim 19, further comprising an elastic device for moving the end stop toward the holding position.

22. The blood collection system of claim 19, further comprising a stop spring for displacing the end stop into the holding position.

23. The blood collection system of claim 22, wherein, during the puncture movement of the lancet in the puncturing direction, the stop spring is pre-stressed and locked, further wherein the stop spring is released at the end of the forward movement of the lancet.

24. The blood collection system of claim 22, wherein the stop spring has a residual tension when the end stop is in its holding position.

25. The blood collection system of claim 22, further comprising a tensioning device configured to apply tension to the stop spring, the tensioning device comprising a threaded rod with a thread and a first tension element that is moved by rotation of the threaded rod, the first tension element configured to be guided on a guide face during its movement to apply tension to the stop spring.

26. The blood collection of claim 25, wherein the threaded rod has first and second threads running in opposite directions and is configured to move the first tension element and a second tension element, respectively, wherein the first tension element applies tension to the stop spring and the second tension element applies tension to the drive spring, whereby the stop spring and the drive spring are configured to be tensioned simultaneously.

27. The blood collection of claim 26, wherein the first thread and the second thread have different pitches.

28. The blood collection system of claim 26, wherein the first tension element is guided on a return edge in its movement opposite the direction of movement for applying tension and becomes disengaged from the stop spring.

29. The blood collection system of claim 18, wherein the drive spring is arranged behind the lancet.

30. The blood collection system of claim 29, wherein the drive spring is coupled to the lancet during the forward and retraction movements.

31. The blood collection system of claim 29, wherein the drive spring is positioned substantially coaxially with the lancet.

32. A blood collection system for collecting blood from a body part for diagnostic purposes, comprising:
    a housing having a lancet guide configured to guide a lancet,
    a lancet drive configured to drive a puncture movement of the lancet, the puncture movement comprising a forward movement in a puncture direction, a reversal point, and a subsequent retraction movement in the direction opposite the puncture direction;
    the lancet drive comprising a drive spring arranged behind the lancet, wherein during the forward movement the drive spring is connected to the lancet to drive the lancet in the puncture direction and wherein the drive spring contracts during the retraction movement, further wherein the lancet is automatically pulled back in the retraction movement by the drive spring immediately upon reaching the reversal point;

an oscillation control device configured to control oscillation of the lancet after the lancet reaches the reversal point, the oscillation control device being engaged and actuated at the end of the forward movement, wherein the forward movement of the lancet before puncture is substantially unaffected by the oscillation control device, the oscillation control device configured to prevent repeated puncturing of the body part by the lancet;

wherein the oscillation control device comprises:
- a movable end stop which is configured to shift into a holding position after the lancet has reached the reversal point;
- a fixing device for securing the end stop in the holding position; and
- a stop spring for displacing the end stop into the holding position;
- wherein, during the puncturing movement of the lancet in the puncture direction, the stop spring is pre-stressed and locked, further wherein the stop spring is released at the end of the forward movement of the lancet.

* * * * *